United States Patent [19]

Papenfuhs et al.

[11] Patent Number: 5,304,655
[45] Date of Patent: Apr. 19, 1994

[54] N'-SUBSTITUTED N-AMINO-3,4,5,6-TETRAFLUOROPHTHALIMIDES, AND PROCESSES FOR THEIR PREPARATION

[75] Inventors: Theodor Papenfuhs, Frankfurt am Main; Ralf Pfirmann, Griesheim, both of Fed. Rep. of Germany

[73] Assignee: Hoechst AG, Frankfurt am Main, Fed. Rep. of Germany

[21] Appl. No.: 126,794

[22] Filed: Sep. 24, 1993

Related U.S. Application Data

[62] Division of Ser. No. 872,058, Apr. 23, 1992, Pat. No. 5,274,115.

[30] Foreign Application Priority Data

Apr. 25, 1991 [DE] Fed. Rep. of Germany ....... 4113461

[51] Int. Cl.$^5$ .......................................... C07D 209/48
[52] U.S. Cl. ..................................... 548/461; 548/475
[58] Field of Search ................................ 548/461, 475

[56] References Cited

PUBLICATIONS

CA 113(6):41523t N-(2-methacryloyloxyethyl) . . . preparation, Kawakami et al., p. 14, 1990.
CA 113(17):152040c Preparation of . . . fluorophthalimides, Kumai et al., p. 741, 1990.
CA 115(25):2798116 Tetrafluoro-N-phenylphthalimide, Nowak et al., p. 993, 1991.

Primary Examiner—Mary C. Lee
Assistant Examiner—Joseph K. McKane
Attorney, Agent, or Firm—Connolly & Hutz

[57] ABSTRACT

Compounds of the formula

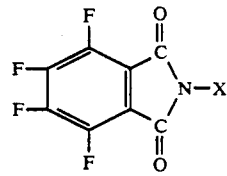

in which X is the radical

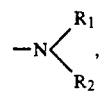

where $R_1$ and $R_2$ are in each case a hydrogen atom, an alkyl-($C_1$-$C_{10}$) group, aryl group, alkyl($C_1$-$C_6$)-CO group or aryl-CO group, where the aryl or aryl-CO group in the case of $R_1$ and $R_2$ can be substituted on the aromatic ring by fluorine and/or chlorine atoms and/or alkyl($C_1$-$C_4$) groups, or $R_1$ and $R_2$ together are a phthaloyl radical which can be substituted on the aromatic ring by 4 chlorine atoms or 4 fluorine atoms, or where X is the radical

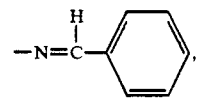

which can be substituted on the aromatic ring by fluorine and/or chlorine atoms and/or alkyl($C_1$-$C_4$) groups, and processes for their preparation.

13 Claims, No Drawings

N'-SUBSTITUTED N-AMINO-3,4,5,6-TETRAFLUOROPHTHALIMIDES, AND PROCESSES FOR THEIR PREPARATION

This application is a divisional of Ser. No. 07/872,058, now U.S. Pat. No. 5,274,115 filed Apr. 23, 1992.

DESCRIPTION

The present invention relates to novel N'-substituted N-amino-3,4,5,6-tetrafluorophthalimides and processes for their preparation. By acid hydrolysis or alcoholysis, the novel compounds can be converted into 2,3,4,5-tetrafluorobenzoic acid, which is an important precursor for the preparation of antibacterial agents [DE-A-3,318,145].

To date, tetrafluorobenzoic acid could be synthesized from tetrachlorophthaloyl chloride (G. G. Yakobson, V. N. Odinkov, N. N. Vorozhtsov, Zh. Obshsh. Khim. 36 (1966), 139; Imperial Chemical Industries PLC, EP 140,482, GB 2,146,635, 24.7.84), from tetrafluoroanthranilic acid (S. Hayashi, N. Ishikawa, Bull. Chem. Soc. Jap. 45 (1972), 2909), from 1,2,3,4-tetrafluorobenzene (L. J. Belf, M. W. Buxton, J. F. Tilney-Bassett, Tetrahedron 23 (1967), 4719; Z. Naturforsch. 31B (1976), 1667), from tetrachlorophthalic anhydride (Bayer AG, DE 3,810,093 A1, 5.10.89; Warner-Lambert Co., EP 218,111, 9.9.86) or from tetrachlorophthalodinitrile (Imperial Chemical Industries PLC, GB 2,134,900, 22.8.84) via steps which were complicated in some cases and/or were impossible to realize technically. The same holds true for the preparation of tetrafluorobenzoic acid from 1,2-dibromotetrafluorobenzene (C. Tamborski, E. J. Soloski, J. Organometallic Chem., 10 (1967), 385) and the method described by P. Sartori and A. Golloch (Chem. Ber. 101 (1968), 2004), starting from tetrafluorophthalic acid. N-carbon-substituted tetrachlorophthalimides were also employed for the synthesis of tetrafluorophthalic acid (SDS Biotech. K.K., EP 259,663, 18.8.87), which can be converted into 2,3,4,5-tetrafluorobenzoic acid.

2,3,4,5-Tetrafluorobenzoic acid can be obtained from tetrafluorophthalic acid or its anhydride by a variety of processes (EP 194,671; EP 218,111; JP 01/025,737; JP 63/295,529). When carrying out some of these processes, reagents are used which are either technically not accessible or ecologically unacceptable. The main problem is mostly that tetrafluorophthalic acid must be isolated before being further reacted, which can cause considerable problems.

There was thus a demand for a better preparation method for the precursor 2,3,4,5-tetrafluorobenzoic acid, which could be satisfied by the fact that N'-substituted N-amino-3,4,5,6-tetrafluorophthalimides can be prepared according to the invention which, in turn, can be converted in a known manner into 2,3,4,5-tetrafluorobenzoic acid, as mentioned above.

The present invention relates to novel N'-substituted N-amino-3,4,5,6-tetrafluorophthalimides of the formula (I)

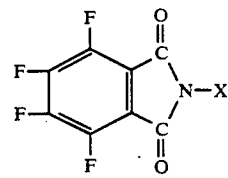

in which X is the radical

where $R_1$ and $R_2$ are in each case a hydrogen atom, an alkyl-$(C_1-C_{10})$ group, aryl group, for example the phenyl group, an alkyl -$(C_1-C_6)$-CO group, for example the acetyl group, an aryl-CO group, for example the benzoyl group, it being possible for the aryl, or aryl-CO, groups in the case of $R_1$ and $R_2$ to be substituted on the aromatic ring for example by fluorine and/or chlorine atoms and/or alkyl-$(C_1-C_4)$ groups, or $R_1$ and $R_2$ together are a phthaloyl radical which can be substituted on the aromatic ring by 4 chlorine atoms or 4 fluorine atoms, preferably the radical

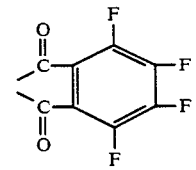

or in which X is the radical

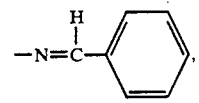

which can be substituted on the aromatic ring for example by fluorine and/or chlorine atoms and/or alkyl-$(C_1-C_4)$ groups, and a process for their preparation, by reacting 1 mol of 3,4,5,6-tetrachlorophthalic anhydride with an at least equimolar amount, expediently a molar excess of up to approximately 20 mol %, of a nitrogen compound of the formula (2)

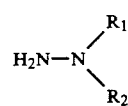

in which $R_1$ and $R_2$ have the abovementioned meanings, in an aqueous/alcoholic medium, in glacial acetic acid, in approximately 90 to 100% strength sulfuric acid or in oleum at temperatures (depending on the medium used) of approximately 100° to approximately 220° C., to give the corresponding N'-substituted N-amino-3,4,5,6-tetrachlorophthalimide of the formula (3)

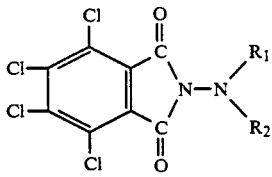

(3)

in which $R_1$ and $R_2$ have the abovementioned meanings, and the resulting imide of the abovementioned formula (3) reacting with potassium fluoride, rubidium fluoride or cesium fluoride or mixtures of these, preferably with potassium fluoride alone, at temperatures of approximately 50° to approximately 230° C., preferably approximately 90° to approximately 140° C., in the presence or absence of a phase-transfer catalyst, in a polar aprotic solvent, directly or after prior reaction with an at least equimolar amount of benzaldehyde which can be substituted on the aromatic ring for example by fluorine and- /or chlorine atoms and/or alkyl-($C_1$-$C_4$) groups, in a manner known per se to give the corresponding benzal compound, or after prior acylation with an alkyl- ($C_1$-$C_6$)-CO halide, preferably an alkyl-($C_1$-$C_6$)-CO chloride, carboxylic anhydride of the formula alkyl(- $C_1$-$C_6$)-CO—O—OC-($C_1$-$C_6$)alkyl, aryl-CO halide, preferably aryl-CO chloride, or phthalic anhydride which can be substituted on the aromatic ring by 4 chlorine atoms or 4 fluorine atoms, in a manner known per se (Halex reaction).

It is evident that in the case where the imide of the formula (3) has previously been reacted with the benzaldehyde which is optionally substituted on the ring, to give the benzal compound of the formula (4)

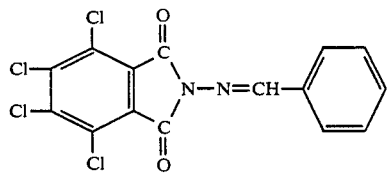

(4)

$R_1$ and $R_2$ in the compounds of the formulae (2) and (3) are both hydrogen atoms, and in the case where the imide of the formula (3) has previously been acylated, at least one of the radicals $R_1$ and $R_2$ in the compounds of the formulae (2) and (3) is a hydrogen atom.

The abovementioned alkali metal fluorides are used in amounts of 100 to approximately 500 mol %, preferably approximately 101 to approximately 150 mol %, particularly preferably approximately 102 to approximately 120 mol % per chlorine atom to be exchanged. In the case of 4 chlorine atoms to be exchanged per molecule, approximately 4.08 to approximately 4.8 equivalents of the abovementioned alkali metal fluorides, if appropriate in the form of a mixture, are particularly preferably used.

Suitable polar aprotic solvents for the fluorination (Halex reaction) are, for example, dimethylformamide, dimethylacetamide, dimethyl sulfoxide, tetramethylene sulfoxide, dimethyl sulfone, diphenyl sulfoxide, diphenyl sulfone, sulfolane, N-methylpyrrolidone or 1,3-dimethylimidazolidin-2-one.

Phase-transfer catalysts which can be used are, for example, quaternary ammonium or phosphonium salts. Suitable compounds which may be mentioned individually are the following: tetraalkyl-($C_1$-$C_{18}$)-ammonium chlorides or tetraalkyl-($C_1$-$C_{18}$)-ammonium bromides, tetraalkyl-($C_1$-$C_{18}$)-phosphonium chlorides or tetraalkyl-($C_1$-$C_{18}$)-phosphonium bromides, tetraphenylphosphonium chloride or tetraphenylphosphonium bromide, [(phenyl)$_m$(alkyl($C_1$-$C_{18}$))$_n$]-phosphonium chlorides or [(phenyl)$_m$(alkyl($C_1$-$C_{18}$))$_n$]-phosphonium bromides, where m is 1 to 3, n is 3 to 1 and m+n is 4.

The phase-transfer catalysts are employed in amounts of approximately 0.1 to approximately 50 mol %, preferably approximately 1 to approximately 20 mol %, particularly preferably approximately 2.5 to approximately 15 mol %, relative to the N'-substituted N-amino-3,4,5,6-tetrachlorophthalimide of the abovementioned formula (3) or (4).

It is preferred to carry out the process in the absence of phase-transfer catalysts.

Oleum, which is optionally employed in the first step, expediently comprises 0 to approximately 50%, preferably approximately 0.5 to approximately 15%, of $SO_3$.

The conversion of the imide of the abovementioned formula (3) with the benzaldehyde which is optionally substituted on the ring, which is optionally carried out prior to the Halex reaction, is carried out in a manner known per se [HOUBEN WEYL, Volume 10/2, pages 89-97, and Volume 11/2, pages 73-85 and 89-99].

The acylation of the imide of the abovementioned formula (3), which is optionally carried out prior to the Halex reaction, can be effected by methods known per se. For example, acyl groups can be introduced by reaction with one or two free hydrogen atoms in the case of $R_1$ and/or $R_2$ of the imide of the formula (3) with acyl halides—preferably acyl chlorides—in an inert solvent such as, for example, water, acidic or alkaline aqueous solutions, methylene chloride, chloroform, toluene, xylenes or chlorobenzene, using approximately 0.8 to approximately 5 base equivalents at temperatures of approximately 0 to approximately 200° C. The reaction can also be carried out using equimolar amounts up to large excesses of acyl anhydrides with or without solvents without the presence of bases at temperatures of approximately 0° to approximately 200° C., preferably approximately 80° to approximately 150° C. Other acylation variants which are also known and mentioned in the references cited below can also be used [HOUBEN WEYL, Methoden der organischen Chemie [Methods in Organic Chemistry], Volume 8, pages 655-661 (1952); Volume 10/2, pages 127-168 (1967); Volume 11/2, pages 3-38 (1958); Volume E5/2, pages 934-1129, in particular pages 932-981 and 1116-1121 (1985)].

The compounds of the abovementioned formula (1) which have been obtained according to the invention can be converted in a manner known per se into 3,4,5,6-tetrafluorophthalic anhydride by hydrolysis with aqueous mineral acid, or in a manner known per se into the corresponding 3,4,5,6-tetrafluorophthalic acid diesters by alcoholysis with alcoholic mineral acid, and these products, in turn, can be converted by methods known from the literature into 2,3,4,5-tetrafluorobenzoic acid by further hydrolysis or by decarboxylation.

Compared with known processes, the essential advantage of the present process is the fact that the starting materials are readily available. In addition, no substantial amounts of hydrogen fluoride are evolved during hydrolysis of the intermediates because no aliphatically bonded fluorine atoms were introduced, which avoids the problem with materials, which is to be expected in some known processes. Furthermore, relatively low reaction temperatures can be used because the reactivity of the tetrachlorinated compounds is high, which is why decomposition reactions are largely avoided.

Mono-, di- and trifluorophthalimides can be prepared analogously.

The process according to the invention can be carried out under atmospheric pressure and under subatmospheric or superatmospheric pressure.

The examples which follow are intended to illustrate the process according to the invention without imposing any restrictions.

EXAMPLE 1

285.9 g (1 mol) of tetrachlorophthalic anhydride and 50.1 g (1 mol) of hydrazine hydrate in 250 ml of water/250 ml of ethanol are heated at the boil for 2 hours. After the ethanol has been removed, the mixture is allowed to cool, and the resulting N-aminotetrachlorophthalimide is subsequently filtered off with suction (yield 266.9 g, 0.89 mol, 89%). This product is stirred for 3 hours at 110° C. with 95.9 g (0.90 mol) of benzaldehyde in 500 ml of glacial acetic acid, during which process the yellow benzal compound is formed which, after cooling, can be filtered off with suction and dried. (Yield 303.9 g, 0.783 mol, 88%.) After the benzal compound has been introduced into 800 ml of sulfolane at 160° C., 206.2 g (3.5 mol) of potassium fluoride are added. After 12 hours at this temperature, all chlorine atoms have been replaced by fluorine atoms, as can be demonstrated by GC check. The mixture is allowed to cool, and the salt is filtered off with suction and washed with sulfolane. After approx. 80% of the sulfolane has been removed at 2-3 torr, the residue (approx. 400 ml) is stirred into 600 ml of water. The solid which has precipitated is filtered off with suction and washed twice using 100 ml portions of water. After drying in vacuo, 161.1 g (0.501 mol; 64%) of N-(N'-benzylidene)aminotetrafluorophthalimide are obtained as a beige, crystalline substance (cis-trans isomer mixture).

Melting point: 179-186° C.

$^1$H NMR (CDCl$_3$, internal standard TMS): $\delta$ = 7.45 (m, 3.2H, AR—H); 7.86 (m, 2.8H, Ar—H); 8.65 (s, 0.63H, —N=CH—); 9.28 (s, 0.57H, —N=CH—)

$^{19}$F NMR (acetone, internal standard CFCl$_3$): $\delta$ = −135.3 (2ddd, 2F); −141.7 (2ddd, 2F)

MS: m/z (%) = 76 (13), 90 (19), 103 (100), 146 (41); 177 (39), 207 (13), 219 (15), 281 (4), 322 (M+, 12)

EXAMPLE 2

285.9 9 (1 mol) of tetrachlorophthalic anhydride and 50.1 g (1 mol) of hydrazine hydrate in 250 ml of water/250 ml of ethanol are heated at the boil for 2 hours. After the ethanol has been removed, the mixture is allowed to cool, and the resulting N-aminotetrachlorophthalimide is subsequently filtered off with suction and reacted with equimolar amounts of tetrachlorophthalic anhydride in boiling glacial acetic acid. N-Tetrachlorophthalimidotetrachlorophthalimide is obtained after cooling and filtration with suction as a colorless, crystalline product in a yield of 91%. 567.8 g (1 mol) of this are suspended in 1.5 l of N,N-dimethylacetamide, and the mixture is heated at 100° C. After a mixture of 500 g (8.6 mol) of potassium fluoride and 50 g (0.32 mol) of cesium fluoride has been added, the mixture is stirred for 5 hours at this temperature, the salt is filtered off with suction, and most of the solvent is stripped off in vacuo. The mixture is transferred into 1 l of water, and the crude product which has precipitated is filtered off with suction and washed twice with 100 ml of water to remove the solvent. 302.3 g (0.693 mol, 69%) of N-tetrafluorophthalimidotetrafluorophthalimide are obtained in the form of ochre crystals, but these can be recrystallized from n-hexane/xylene to give colorless crystals.

Melting point: 311-312° C.

$^{19}$F NMR (acetone, internal standard CFCl$_3$): $\delta$ = −135.0 (ddd, 4F); −142.6 (ddd, 4F)

IR [cm$^{-1}$]: v=(s) 1760, 1510, 1405, 1285, 1080, 950, 740, 625; (w) 1645, 1320, 1160, 1145, 1120, 915

MS: m/z (%) = 79 (3), 98 (9), 148 (69), 176 (70), 202 (6), 281 (1), 324 (3), 373 (3), 392 (28), 436 (M+, 100)

EXAMPLE 3

285.9 g (1 mol) of tetrachlorophthalic anhydride and 60.1 g (1 mol) of N,N-dimethylhydrazine in 500 ml of glacial acetic acid are heated at 60° C. for 4 hours. The cold suspension is filtered off with suction, and the product is dried in vacuo, giving 309.8 g (0.945 mol) of N',N'-dimethylaminotetrachlorophthalimide, which is taken up in 800 g of N-methylpyrrolidone and kept for 4 hours at 160° C. in a mixture of potassium fluoride and cesium fluoride (280.9 g, 4.54 mol). The salt of the reaction is subsequently filtered off with suction, and most of the solvent (550 g) is removed in vacuo. After the residue has been treated with 900 g of water, the solid which has precipitated is filtered off and gives, after drying, 173.5 g (0.662 mol, 70%) of N,N-dimethylaminotetrafluorophthalimide in the form of a beige solid.

Melting point: 184-189° C.

$^1$H NMR (CDCl$_3$, internal standard TMS): $\delta$ = 3.00 (s, 6H, —N(CH$_3$)$_2$)

$^{19}$F NMR (CDCl$_3$, internal standard CFCl$_3$): $\delta$ = −135.8 (ddd, 2F); −142.5 (ddd, 2F)

MS: m/z (%) = 43 (100), 76 (6), 98 (9), 148 (34), 176 (10), 202 (22), 221 (41), 262 (M+, 22)

We claim:

1. A process for the preparation of a compound of the formula (1)

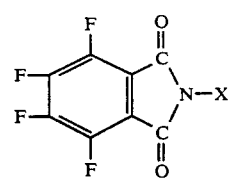

in which X is the radical

where R$_1$ and R$_2$ are in each case a hydrogen atom, an alkyl-(C$_1$–C$_{10}$) group, aryl group, alkyl(C$_1$–C$_6$)-CO group or aryl-CO group, where the aryl or aryl-CO groups in the case of R$_1$ and R$_2$ can be substituted on the aromatic ring by fluorine and/or chlorine atoms and/or alkyl(C$_1$–C$_4$) groups, or R$_1$ and R$_2$ together are a phthaloyl radical which can be substituted on the aromatic ring by 4 chlorine atoms or 4 fluorine atoms, or in which X is the radical

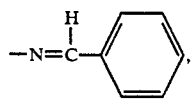

which can be substituted on the aromatic ring by fluorine and/or chlorine atoms and/or alkyl($C_1$–$C_4$) groups, which comprises reacting 1 mol of 3,4,5,6-tetrachlorophthalic anhydride with an at least equimolar amount of a nitrogen compound of the formula (2)

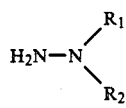

in which $R_1$ and $R_2$ have the abovementioned meanings, in an aqueous/alcoholic medium, in glacial acetic acid, in approximately 90 to 100% strength sulfuric acid or in oleum at temperatures (depending on the medium used) of approximately 100° to approximately 200° C., to give the corresponding N'-substituted-N-amino-3,4,5,6-tetrachlorophthalimide of the formula (3)

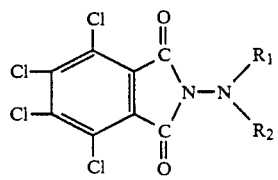

in which $R_1$ and $R_2$ have the abovementioned meanings, and reacting the resulting imide with potassium fluoride, rubidium fluoride or cesium fluoride or mixtures of these at temperatures of approximately 50° to approximately 230° C. in the presence or absence of a phase-transfer catalyst, in a polar aprotic solvent, directly or after prior reaction with an at least equimolar amount of benzaldehyde which can be substituted on the aromatic ring by fluorine and/or chlorine atoms and/or alkyl(-$C_1$–$C_4$) groups to give the corresponding benzal compound, or after prior acylation with an alkyl ($C_1$–$C_6$)-CO halide, carboxylic anhydride of the formula alkyl(-$C_1$–$C_6$)-CO—O—OC-($C_1$–$C_6$)alkyl, aryl-CO halide or phthalic anhydride which can be substituted on the aromatic ring by 4 chlorine atoms or 4 fluorine atoms.

2. The process as claimed in claim 1, wherein the reaction with potassium fluoride, rubidium fluoride or cesium fluoride, or mixtures of these, is carried out at temperatures of approximately 90° to approximately 140° C.

3. The process as claimed in claim 1, wherein the abovementioned alkali metal fluorides are employed in amounts of 100 to approximately 500 mol % per chlorine atom to be exchanged.

4. The process as claimed in claim 1, wherein the fluorination is carried out in dimethylformamide, dimethylacetamide, dimethyl sulfoxide, tetramethylene sulfoxide, dimethyl sulfone, diphenyl sulfoxide, diphenyl sulfone, sulfolane, N-methylpyrrolidone or 1,3-dimethylimidazolidin-2-one as polar aprotic solvent.

5. The process as claimed in claim 1, wherein the fluorination is carried out in the presence of a quaternary ammonium or phosphonium salt as phase-transfer catalyst.

6. The process as claimed in claim 1, wherein the fluorination is carried out in the presence of tetraalkyl(-$C_1$–$C_{18}$)-ammonium chlorides or tetraalkyl($C_1$–$C_{18}$)ammonium bromides, tetraalkyl($C_1$–$C_{18}$)phosphonium chlorides or tetraalkyl($C_1$–$C_{18}$)phosphonium bromides, tetraphenylphosphonium chloride or tetraphenylphosphonium bromide, [(phenyl)$_m$(alkyl($C_1$–$C_{18}$))$_n$]-phosphonium chlorides or [(phenyl)$_m$(alkyl($C_1$–$C_{18}$))$_n$]-phosphonium bromides, where m is 1 to 3, n is 3 to 1 and m+n is 4, as phase-transfer catalysts.

7. The process as claimed in claim 1, wherein the phase-transfer catalysts are employed in amounts of approximately 0.1 to approximately 50 mol %, based on the N'-substituted N-amino-3,4,5,6-tetrachlorophthalimide.

8. The process as claimed in claim 1, wherein the pressure at which it is carried out is atmospheric pressure, superatmospheric pressure or subatmospheric pressure.

9. The process as claimed in claim 1, wherein after said compound of the formula (1) is formed, the compound is subjected to hydrolysis to form 3,4,5,6-tetrafluorophthalic anhydride, or is subjected to alcoholysis with an alcoholic mineral acid to form 3,4,5,6-tetrafluorophthalic acid diester, and further wherein said 3,4,5,6-tetrafluorophthalic anhydride or 3,4,5,6-tetrafluorophthalic acid diester is converted to 2,3,4,5-tetrafluorobenzoic acid by further hydrolysis or by decarboxylation.

10. The process as claimed in claim 1, wherein $R_1$ is a hydrogen atom, an alkyl ($C_1$–$C_{10}$) group, a phenyl group, an alkyl ($C_1$–$C_6$)-CO group or a benzoyl group and $R_2$ is a phenyl group or a benzoyl group, where the phenyl or benzoyl groups in the case of $R_1$ and $R_2$ can be substituted on the aromatic ring by at least one of fluorine atoms, chlorine atoms and alkyl ($C_1$–$C_4$) groups.

11. The process as claimed in claim 1, wherein $R_1$ and $R_2$ together are a phthaloyl radical having the formula

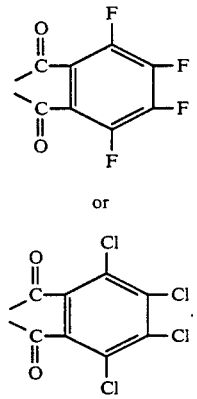

12. The process as claimed in claim 1, wherein $R_1$ is a hydrogen atom, an alkyl ($C_1$–$C_{10}$) group, a phenyl group, an alkyl ($C_1$–$C_6$)-CO group or a benzoyl group and $R_2$ is an alkyl ($C_1$–$C_6$)-CO group.

13. The process as claimed in claim 1, wherein X is the radical

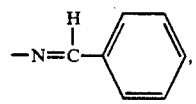

which can be substituted on the aromatic ring by at least one of fluorine atoms, chlorine atoms and alkyl ($C_1$–$C_4$) groups.

* * * * *